(12) United States Patent
Astrom et al.

(10) Patent No.: US 7,989,215 B2
(45) Date of Patent: Aug. 2, 2011

(54) METHODS AND SYSTEMS FOR ADDING A REAGENT TO AN ANALYTE IN A GEL

(75) Inventors: Jonas Astrom, Uppsala (SE); Bengt Bjellqvist, Uppsala (SE); Lars Fagerstam, Uppsala (SE); Kristina Uhlen, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 713 days.

(21) Appl. No.: 11/917,930

(22) PCT Filed: Jun. 9, 2006

(86) PCT No.: PCT/EP2006/005531
§ 371 (c)(1),
(2), (4) Date: Feb. 5, 2008

(87) PCT Pub. No.: WO2006/136297
PCT Pub. Date: Dec. 28, 2006

(65) Prior Publication Data
US 2010/0143895 A1    Jun. 10, 2010

(30) Foreign Application Priority Data

Jun. 18, 2005  (GB) .................... 0512513.3
Apr. 25, 2006  (GB) .................... 0608147.5

(51) Int. Cl.
*G01N 27/26*    (2006.01)
*G01N 27/447*   (2006.01)
*B01D 57/02*    (2006.01)
*C07K 1/26*     (2006.01)

(52) U.S. Cl. ........ 436/178; 204/456; 204/465; 204/466; 204/615; 436/86; 436/87; 436/94; 436/174; 435/18; 435/23; 435/24

(58) Field of Classification Search .................. 204/456, 204/459–462, 613, 465–466, 615–616; 435/18, 435/23–24, 195, 199, 212–213, 219, 287.1–287.3; 436/86–87, 94, 173–175, 178
See application file for complete search history.

(56) References Cited

U.S. PATENT DOCUMENTS 3,378,347 A * 4/1968 Saravis .................... 422/58
(Continued)

FOREIGN PATENT DOCUMENTS

AU    2003200406    8/2003
(Continued)

OTHER PUBLICATIONS

Aebersold, R., et al., "Mass spectrometry-based proteomics". Nature (2003) 422, 198-207.
(Continued)

*Primary Examiner* — Arlen Soderquist
(74) *Attorney, Agent, or Firm* — Yonggang Ji (57) ABSTRACT

The present invention relates to methods and systems for adding a reagent to an analyte in a gel. The invention further provides methods and systems for transferring liquid analyte reagent mixtures from a gel to a second vessel, such as a microtitre plate. The invention is useful in the manipulation of biological molecules such as nucleic acids, carbohydrates, proteins and peptides. In particular, the invention has utility for manipulating proteins and peptides in isoelectric focusing gels.

23 Claims, 10 Drawing Sheets

U.S. PATENT DOCUMENTS

| | | | | |
|---|---|---|---|---|
| 3,631,575 | A | | 1/1972 | Farris |
| 3,888,759 | A | * | 6/1975 | Elson et al. ............... 204/620 |
| 3,932,229 | A | * | 1/1976 | Grandine ................. 204/466 |
| 4,039,247 | A | * | 8/1977 | Lawman et al. ........... 359/398 |
| 4,181,594 | A | | 1/1980 | Rizk et al. |
| 4,713,349 | A | * | 12/1987 | Levin ....................... 436/515 |
| 4,827,780 | A | * | 5/1989 | Sarrine et al. .......... 73/864.21 |
| 4,834,946 | A | * | 5/1989 | Levin ....................... 422/101 |
| 5,100,626 | A | * | 3/1992 | Levin ....................... 422/100 |
| 5,217,591 | A | | 6/1993 | Gombocz et al. |
| 5,217,592 | A | * | 6/1993 | Jones ....................... 204/614 |
| 5,245,185 | A | * | 9/1993 | Busch et al. ............... 250/288 |
| 5,340,449 | A | | 8/1994 | Shukla |
| 5,585,275 | A | * | 12/1996 | Hudson et al. ............ 436/518 |
| 5,800,785 | A | * | 9/1998 | Bochner ................... 422/101 |
| 5,840,169 | A | | 11/1998 | Andersen |
| 6,165,541 | A | * | 12/2000 | Merchant et al. .......... 427/2.11 |
| 6,231,813 | B1 | * | 5/2001 | Ally et al. ................. 422/100 |
| 6,342,143 | B1 | | 1/2002 | Minden |
| 7,364,897 | B2 | * | 4/2008 | Heaney et al. ........... 435/287.2 |
| 7,645,369 | B2 | * | 1/2010 | Hoeltke et al. ............ 204/451 |
| 7,736,594 | B1 | * | 6/2010 | Grudzien et al. .......... 422/102 |
| 2002/0096431 | A1 | | 7/2002 | Sevigny et al. |
| 2002/0146832 | A1 | | 10/2002 | Michel et al. |
| 2004/0178073 | A1 | | 9/2004 | Kozulic |

FOREIGN PATENT DOCUMENTS

| | | |
|---|---|---|
| EP | 0 382 426 | 8/1990 |
| EP | 1 048 949 | 11/2000 |
| WO | 99/22228 | 5/1999 |
| WO | 00/77510 | 12/2000 |
| WO | 02/071072 | 9/2002 |
| WO | 2004/044574 | 5/2004 |
| WO | WO2004/063739 | 7/2004 |
| WO | WO 2005/029061 | 3/2005 |

OTHER PUBLICATIONS

Breci, L., et al., "Comprehensive proteomics in yeast using chromatographic fractionation, gas phase fractionation, protein gel electrophoresis, and isoelectric focusing". Proteomics (2005) 5, 2018-2028.

Buzas, Z., et al., "Direct vertical electroelution of protein from a PhastSystem band for mass spectrometric identification at the level of a few picomoles". Proteomics (2001) 1, 691-698.

Cargile, B., et al., "Immobilized pH gradients as a first dimension in shotgun proteomics and analysis of the accuracy of pI predictability of peptides". Electrophoresis (2004) 25, 936-945.

Gevaert, K., et al., "Exploring proteomes and analyzing protein processing by mass spectrometric identification of sorted N-terminal peptides". Nature Biotechnology (2003) 21, 566-569.

Gombocz, E., et al., "Electroelution of nonfluorescent stacked proteins detected by fluorescence optics from gel electrophoretic bands for transfer into mass spectrometry". Electrophoresis (2000) 21, 846-849.

Heller, M., et al., "Two-stage Off-Gel isoelectric focusing: Protein followed by peptide fractionation and application to proteome analysis of human plasma". Electrophoresis (2005) 26, 1174-1188.

Michel, P., et al., "Protein fractionation in a multicompartment device using Off-Gel(TM) isoelectric focusing". Electrophoresis (2003) 24, 3-11.

Peng, J., et al., "Evaluation of Multidimensional Chromatography Coupled with Tandem Mass Spectrometry (LC/LC-MS/MS) for Large-Scale Protein Analysis: The Yeast Proteome". Journal of Proteome Research (2003) 2, 43-50.

Sinha, P., et al., "Isoelectric focusing of basic proteases in immbolized pH gradients". Journal of Biochemical and Biophysical Methods (1987) 15, 199-206.

Washburn, M., et al., "Large-scale analysis of the yeast proteome by multidimensional protein identification technology". Nature Biotechnology (2001) 19, 242-247.

Yefimov, S., et al., "Sequential electroelution and mass spectroscopic identification of intact sodium dodecyl sulfate-proteins labeled with 5(6)-carboxyfluorescein-N-hydroxysuccinimide ester". Electrophoresis (2001) 22, 2881-2887.

Yi, E., et al., "Increased quantitative proteome coverage with 13C/12C-based, acid-cleavable isotope-coded affinity tag reagent and modified data acquisition scheme". Proteomics (2005) 5, 380-387.

Zuo, X., et al., "Microscale Solution Isoelectrofocusing". Methods in Molecular Biology, vol. 244: Protein Purification Protocols: Second Edition (2004) 361-375.

* cited by examiner

METHODS AND SYSTEMS FOR ADDING A REAGENT TO AN ANALYTE IN A GEL

The present invention relates to methods and systems for adding a reagent to an analyte in a gel, in particular methods and systems for adding a reagent to gels which have been used to separate biological molecules such as peptides, proteins, carbohydrates or nucleic acids.

BACKGROUND TO THE INVENTION

The separation of biological molecules, such as proteins, peptides and nucleic acids, prior to or in parallel with their identification and quantification, can be achieved by a variety of techniques. Gel electrophoresis is a technique which is commonly used to separate these biological molecules on the basis of their size and/or their charge.

Mass spectrometry has today become the method of choice for the determination of the identity and composition of proteins and peptides. To allow collection of the information required a protein is in a first step cut up into peptides by either enzymatic or chemical means. The most common approach is enzymatic digestion using enzyme(s) which cut the protein at specific amino acid residues, a typical example being trypsin which hydrolyses the protein after lysine or arginine residues. It is, when tryptic digestion is carried out on a sample containing a very limited number of proteins, possible to determine the identity of the protein present from the masses of the peptides resulting from the digestion. A second approach used for identification purposes is the generation of a collision induced secondary mass spectra ion from ions separated in a primary mass spectrum. As the secondary mass spectra contains information on the masses of the amino acid residues constituting a peptide, these masses in combination with the mass of the ion selected in the primary spectrum can be used for identification of the tryptic peptide and the protein corresponding to this peptide. Evidently MS/MS spectra can be used not only for the identification and characterisation of enzymatically digested peptides, but also for peptides originally present in the biological sample. In proteomic studies it is common to use MS or MS/MS not only for identification of protein but also for relative quantification (Aebersold et al; Nature, 2003, 422, 198-207).

A sample applied to a MALDI-MS target is only allowed to contain a limited number of peptides and similarly ESI-MS can only accept a limited number of peptides per time unit. The sample is normally a very complex mixture containing many thousand of proteins which after digestion could easily correspond to one hundred thousand to more than one million peptides. There is therefore a need for rigorous separation of the peptides prior to MS characterisation and quantification. A variety of different separation methods including electrophoretic and chromatographic methods can be used; normally multiple separation steps are required.

Separation can be conducted solely at the protein level prior to tryptic digestion. A typical example of this approach is two-dimensional (2-D) electrophoresis. Alternatively, separation can be carried out at the protein level in the first step, followed by digestion and finally separation of the resulting peptides prior to MS. One example of this approach uses reverse phase chromatography (RPC) at the protein level followed by digestion and reverse phase chromatography separation of resulting peptides prior to ESI MS/MS. Another approach described is SDS-electrophoresis at the protein level followed by digestion and RPC (Breci et al; Proteomics, 2005, 5, 2018-2028). Finally tryptic digestion can be carried out prior to multidimensional separation at the peptide level. Approaches of this type include MudPit (Washburn et al; Nat Biotechnol., 2001, 19, 242-247), more conventional ion-exchange chromatography followed by RPC (Peng et al; Journal of Proteome Research, 2003, 2, 43-50) as well as peptide isoelectric focusing (IEF) followed by RPC (Cargile et al; Electrophoresis, 2004, 25, 936-945).

When tryptic digestion is the first step, an alternative approach is to decrease the complexity of the sample by the use of methods which allow the selection of a small fraction of the peptides (e.g. iCAT [Aebersold et al; Proteomics, 2005, 5, 380-387] alt COFRADIC [Vandekerckhove et al; Nat Biotechnol., 2003, 21, 566-569]).

Generally electrophoretic techniques like IEF and SDS electrophoresis give, when used at the protein level in gel, much better resolution and protein yields than chromatographic alternatives. 2-D electrophoresis based on the combination of these two techniques, IEF and SDS, is also a commonly used approach when separation of very complex samples is conducted at the protein level. The disadvantages with electrophoretic techniques are however that they are labour intensive, often demand craftsmanship and that they are hard to automate.

Problems can also be encountered extracting the analyte from the gel.

The processing of gel fractions containing peptides, proteins, carbohydrates or nucleic acids from electrophoretic gels in order to facilitate further separation or to enable analyte analysis presents significant difficulties to the operator. Where the gel is present on a glass or plastic plate, individual bands or fractions must be blotted or scraped from the plate, typically with a spatula or sharp knife, and carefully transferred either to a second gel or a reaction vessel for further analysis. In the situation where the gel is supported on a plastic sheet, as with an IPG strip, the strip must be carefully cut with scissors or a sharp blade into a series of pieces which can then be transferred to another gel or reaction vessel for further processing/analysis.

Automatic sampling systems are known for removing bands or spots from gels, such as those described in WO 02/071072. In fact, 2-D electrophoresis frequently employs automatic spot pickers in which gels are generally stained to detect the protein or peptide samples. However, these systems usually involve aspiration of the gel into a pipette which leads to losses due to gel sticking to the outside or inside of the pipette. Furthermore, these systems are labour intensive and time consuming, involving protein/peptide staining and careful use of the apparatus to avoid losses and contamination.

It will be understood by the skilled person that the process of removing bands or fractions of gel manually from a plate or strip is time consuming as painstaking care must be taken in order to ensure that the gel is divided evenly into the appropriate number of fractions, that there is quantitative recovery of the analyte from the gel, and that cross-contamination from 'dirty' instruments used in the transfer process is avoided. The problem of cross-contamination is particularly significant where the analyte has been separated using IPG strips and scissors or a scalpel is used to cut the strip into bands for further processing/analysis, as the blades of these instruments must be thoroughly cleaned before the next band of gel is excised from the strip. Furthermore, such processes generally involve the additional step of pre-staining the gel in order to detect peptides or proteins, such systems are extremely labour intensive.

It will also be understood by the skilled person that the problems described above experienced in removing and transferring gel bands from a plate or IPG strip to a second gel or reaction vessel for further processing will be exacerbated with an increasing number of bands or fractions. Thus, for example, where an IPG strip has to be divided into some 50 pieces and each of the 50 pieces transferred to another gel or a reaction vessel, there is an increasing likelihood of cross-contamination and poor recoveries.

To avoid the problem with sample extraction from gels, isoelectric focusing separation can be carried out in liquid phase (Zuo et al.; Methods Mol Biol., 2004, 244, 361-75). The equipment used by Zuo et al. comprises a series of chambers separated by membranes titrated to specific pH-values. However, one disadvantage of this approach is that peptides and proteins have low solubility in the vicinity of their isoelectric points; the resulting precipitation and aggregation can lead to problems of poor resolution of the peptides and proteins during the isoelectric focusing.

Michel et al. (Electrophoresis, 2003, 24, 3-11) describe a technique which allows the fractionation of complex biological samples according to their isoelectric point (pI) as well as the direct recovery of the compounds for further analysis. The technique, termed 'off-gel IEF', involves dividing IPG strips into a series of wells using a multiwell device which is open at both ends, adding protein sample in an IPG buffer and then conducting electrophoresis to separate the protein mixture. The content of each well is then removed for protein analysis by mass spectrometry and the technique shown to effect a resolution of 0.1 pH units. However, as in the approach of Zuo et al. discussed above, the proteins are present in liquid phase during focusing which increases the risk of precipitation and aggregation. With the geometry resulting from the approach of Michel et al., the proteins will be present in a region with much lower electric field than would be the case if the focusing was done solely in the gel in the absence of any solution added in the multiwell device. Compared to conventional gel focusing the result is lower resolution and a demand for longer focusing times.

The same group (Heller et al.; Electrophoresis, 2005, 26, 1174-1188) has recently reported the use of 'off-gel IEF' for the separation and identification of proteins and their isoforms by use of a two-stage process, the first involving separation of the proteins and their isoforms on the basis of their pI's and the second the separation and identification of the trypsinized peptide fragments.

IEF can also be carried out in configurations where separated proteins are collected in solution in chambers separated with membranes (Righetti et al; J. Biochem. Biophys. Meth., 1987, 15, 199-206). This approach is also limited by the fact that proteins close to their isoelectric point tend to aggregate and precipitate.

Other systems have been disclosed which describe methods for processing proteins in gels wherein gel fragments containing proteins are isolated from the gel, subjected to proteolytic digestion and then the cleavage peptides produced are identified. Such an automated system is described in WO 02/071072, in which isolated protein-gel fragments are directly transferred to a corresponding number of reaction vessels of a first microtitre plate by a robotic arm device, the base of the microtitre plate having a hydrophobic filter membrane, and incubated with a protease. Following hydrolysis, the peptide products are filtered through the hydrophobic filter membrane into a second microtitre plate and concentrated for subsequent analysis.

Thus electrophoretic separation in gel provides outstanding resolution but, as discussed above, often involves problems with sample transfer from the gel to liquid phase and is difficult to automate.

It is therefore an object of the present invention to provide methods and systems which facilitate the preparation of gel fractions and enable the further processing and manipulation thereof while ameliorating the problems encountered in the prior art. Another object of the invention is to provide such methods and systems without the need to pre-stain gels for the detection of such analytes. A further object of the present invention is to provide methods and systems for adding reagents to gel fractions and for eluting analyte, either prior to or following chemical or enzymatic modification, from a gel.

SUMMARY OF THE INVENTION

According to a first aspect of the present invention, there is provided a method for adding a reagent to an analyte in a gel comprising the steps of
i) moving a multiwell template onto said gel,
wherein said multiwell template comprises a body having a plurality of open-ended chambers, each said chamber being defined by one or more walls,
to form a plurality of wells between the gel and the one or more said walls, and
ii) optionally, subjecting said analyte to a chromatographic or electrophoretic separation within the gel, and
iii) adding a liquid reagent to the one or more of said wells to form a liquid analyte reagent mixture,
wherein the reagent is capable of solubilising the analyte or modifying the analyte or its environment.

Suitably, the reagent is a buffer; the pH of the buffer may be varied depending upon the particular analyte.

Suitably, the reagent is an acid or an alkali. The acid or alkali may modify the analyte or the environment in which it is present.

Suitably, the reagent is an enzyme. Preferably, the enzyme is a hydrolase. More preferably, the enzyme is a nuclease or a protease. Most preferably, the enzyme is a protease.

Suitably, the reagent is a detectable moiety. Such detectable markers may, for example, have an isotopic or fluorescent label.

Suitably, the gel is supported on a sheet.

Suitably, the method additionally comprises the step of positioning the gel or said sheet onto a base plate. This base plate could, for example, correspond to a cooling plate of an horizontal electrophoretic apparatus.

Suitably, the method additionally comprises the step of placing the gel or sheet within a retainer.

Suitably, the method additionally comprises the step of positioning said gel or sheet or retainer onto said base plate in a predefined position. Preferably, the base plate additionally comprises one or more recesses and/or protusions on a single surface for locating the gel or the sheet or retainer for the gel or the sheet on said surface.

Suitably, said retainer comprises one or more recesses or protusions on one surface for receipt of the gel or the sheet thereon. Preferably, said one or more recesses or protusions of the retainer additionally comprises locating means for positioning the sheet thereon.

Suitably, the method additionally comprises the step of inserting the multiwell template into an opening in a top plate.

Suitably, the method additionally comprises the step of affixing a securing strip over the end of the multiwell template located within the top plate, said strip comprising a plurality of openings corresponding to the positions of the open-ended chambers in the template.

Preferably, the base plate and/or the top plate and/or the securing strip additionally comprise fastening means for positioning the plurality of wells formed on the gel in a predefined position relative to the base plate and the top plate. More preferably, said fastening means comprises a threaded screw bore in the base plate and an opening suitable for a screw in the top plate and the securing strip.

Preferably, the gel is a polyacrylamide gel. More preferably, the gel is a SDS gel or an isoelectric focusing gel.

Suitably, the body of the multiwell template is divided into a first portion and a second portion, said first portion being shaped for insertion into the opening in the top plate and a second portion being tapered to a base for moving onto the gel. Preferably, the first and second portion are separated by a flange for supporting the multiwell template within the opening in the top plate.

Suitably, the analyte is a peptide, protein, nucleic acid or carbohydrate. Preferably, the analyte is a protein or peptide.

Preferably, the multiwell template is moved onto the gel following the chromatographic or electrophoretic separation of the analyte within the gel. However, under some circumstances it may be preferable to move the multiwell template onto the gel prior to subjecting the analyte to a chromatographic or electrophoretic separation within the gel. In this situation, it will be understood that the chromatographic or electrophoretic separation will have been completed prior to the addition of the liquid reagent to one or more of the wells generated by the multiwell template and the gel.

Suitably, the liquid reagent is added by manual means such as by use of a pipette.

Suitably, the method further comprises the step of transferring the liquid analyte reagent mixture to a second vessel by either manual or automatic means. An example of manual means includes manually operated pipettes, whilst examples of automatic means include automated or programmable liquid handling devices.

Preferably, said second vessel is a well in a microtitre plate.

Suitably, the reagent is added by an automatic liquid handling device and/or the liquid analyte reagent mixture is transferred by an automatic liquid handling device. Preferably, the automatic liquid handling device is under the control of a computer.

According to a second aspect of the present invention, there is provided a system for carrying out the method as hereinbefore described, comprising
  i) a multiwell template comprising a body having a plurality of open-ended chambers, each said chamber being defined by one or more walls; and
  ii) an automatic liquid handling device.

Preferably, the system is under the control of a computer.

BRIEF DESCRIPTION OF THE INVENTION

The method and system of the invention will now be described by reference to the following Figures in which:

FIGS. 5a & b illustrate different features of a multiwell template used in the method of the invention wherein

DETAILED DESCRIPTION OF THE INVENTION

Figure 1:
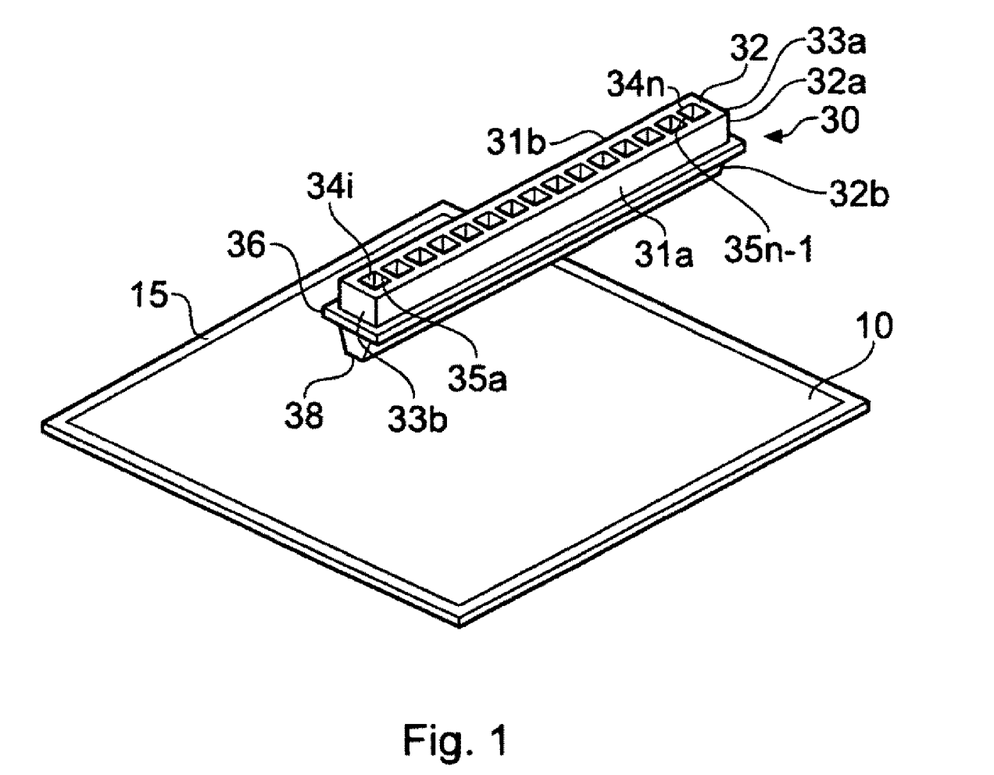
FIG. 1 shows an apparatus which can be used to carry out the method of the invention.

Reagent can be added to an analyte present in a gel (10), in accordance with the claimed method, by using the multiwell template (30) shown in FIG. 1. The diagram shows a multiwell template (30), made of a suitable material such as plastic or metal, positioned above a polyacrylamide gel (10) which is supported on a sheet (15) which may be made, for example, of plastic or glass. The gel (10) contains an analyte which has typically undergone electrophoretic separation. Thus, for example, the gel may contain proteins or peptides. The multiwell template (30) consists of an elongated body (32) having two elongated side walls (31a, b) joined at their ends by two end walls (33a, 33b). A plurality of open-ended chambers (34 i-n) are arranged along the longitudinal axis of the body (32), side chambers being separated from their neighbour(s) by intermediate walls (35a-35n-1), each of which extends from side wall 31a to side wall 31b. The shape of each chamber (34) may vary, for example being circular, oval, polygonal, square or rectangular (as shown).

The multiwell template (30) is moved onto the gel (10), such that the tapered portion (32b) of the body of the template compresses the gel (10) so that the base (38) of the template comes into close proximity to the sheet supporting the gel (10). In this position, a well is defined with the gel or plastic sheet forming the base and the walls of the template defining the walls of the well.

A liquid reagent, such as a buffer or a protease enzyme solution, is added to one or more of the wells (34), to form a liquid analyte reagent mixture. The reagent may solubilise the analyte, as for example in the case of a buffer, or it may modify the analyte (as, for example, in the case of a protease and a protein), or it may modify the environment in which the analyte is present (as for example in the case of an acid).

Figure 2:
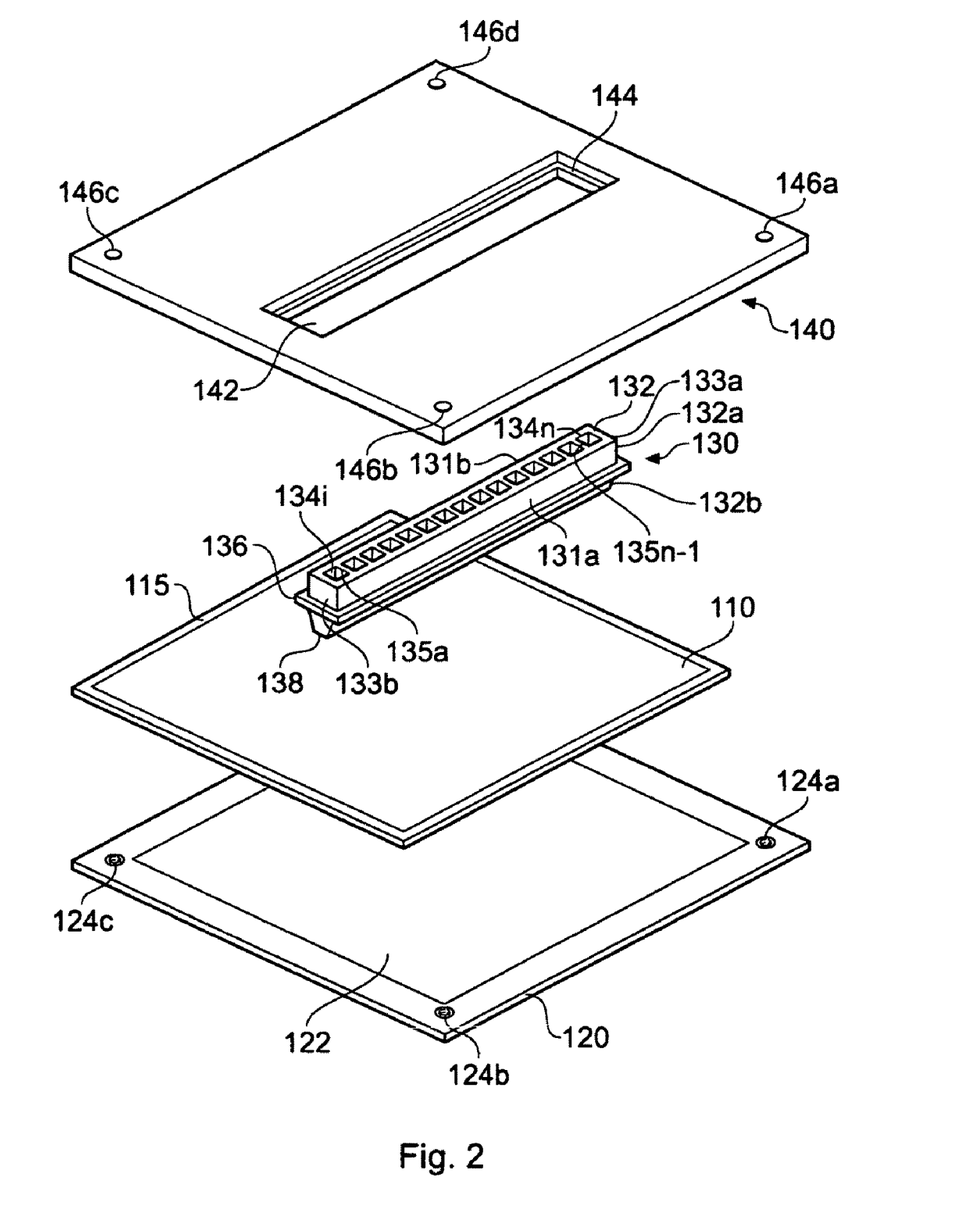
FIG. 2 shows an apparatus which can be used for adding a reagent to an analyte present in a SDS gel.

A diagram of another apparatus which can be used to add a reagent to an analyte in a gel is shown in FIG. 2. The gel (110), such as an SDS gel, is present on the surface of the sheet (115). The sheet (115) is positioned on a base plate (120), made of a plastic or metal material, which has a recess (122) for locating the sheet in a predefined position relative to the plate (120). Fastening means, in the form of threaded screw bores (124 a-c, 124d not shown), are located at each corner of the plate (120) to allow affixing by screws (not shown) of the base plate (120) to a top plate (140) in a predefined position. It will be understood that other forms of fastening means can be used (e.g. clasps, clamps, pins and holes, snap fastening).

A plurality of wells is formed on the gel by means of a multiwell template (130) which may be made of any suitable material such plastic, a metal, ceramic or composite material. The multiwell template (130) consists of an elongated body (132) having two elongated side walls (131a, 131b) joined at their ends by two end walls (133a, 133b). A plurality of open-ended chambers (134 i-n) are arranged along the longitudinal axis of the body (132), side chambers being separated from their neighbour(s) by intermediate wall (135a-135n-1), each of which extends from side wall 131a to side wall 131b. Each chamber (134) may take any appropriate shape, for example circular, oval, polygonal, square or rectangular (as shown).

The body (132) of the multiwell template (130) is divided by a flange (136) into a first (132a) and second (132b) portion; the first (132a) portion being shaped for insertion into an opening (142) in the top plate (140) and a second portion (132b) being tapered to a base (138) for compressing the gel. It will be understood that when the template (130) is lowered or pushed onto the gel (110) and contacts, or comes into close proximity with, the sheet (115) supporting the gel (110), each chamber (134) forms a well with the gel or sheet forming a base and the walls of the chamber (not shown) defining the walls of the well. In this way a plurality of wells are created on the gel. The multiwell template (130) may be inserted into an opening (142) in a top plate (140), which is composed of a plastic or metal (e.g. stainless steel) material, either before or after it has been lowered or pushed onto the gel to form a plurality of wells thereon. In the example shown, the flange (136) supports the template (130) on the ledge (144) of the top plate (140). It should be noted that the template does not cut the gel but rather compresses it to form a plurality of wells. The wells are held in a predefined position relative to the base plate (120) and the top plate (140) by affixing the top plate (140) to the base plate (120) by fastening means in the top (146 a-d) and base (124 a-d) plates. In the example of FIG. 2, screws (not shown) are used to secure the top plate (140) to the base plate (120) by insertion through openings in the top plate (146 a-d) and into the screw bores (124a-d) in the base plate (120). In this way the plurality of wells formed in the gel is held in a predefined position relative to the top and bottom plate. A liquid reagent can then be added to the one or more wells to form a liquid analyte reagent mixture as described above.

Figure 3:
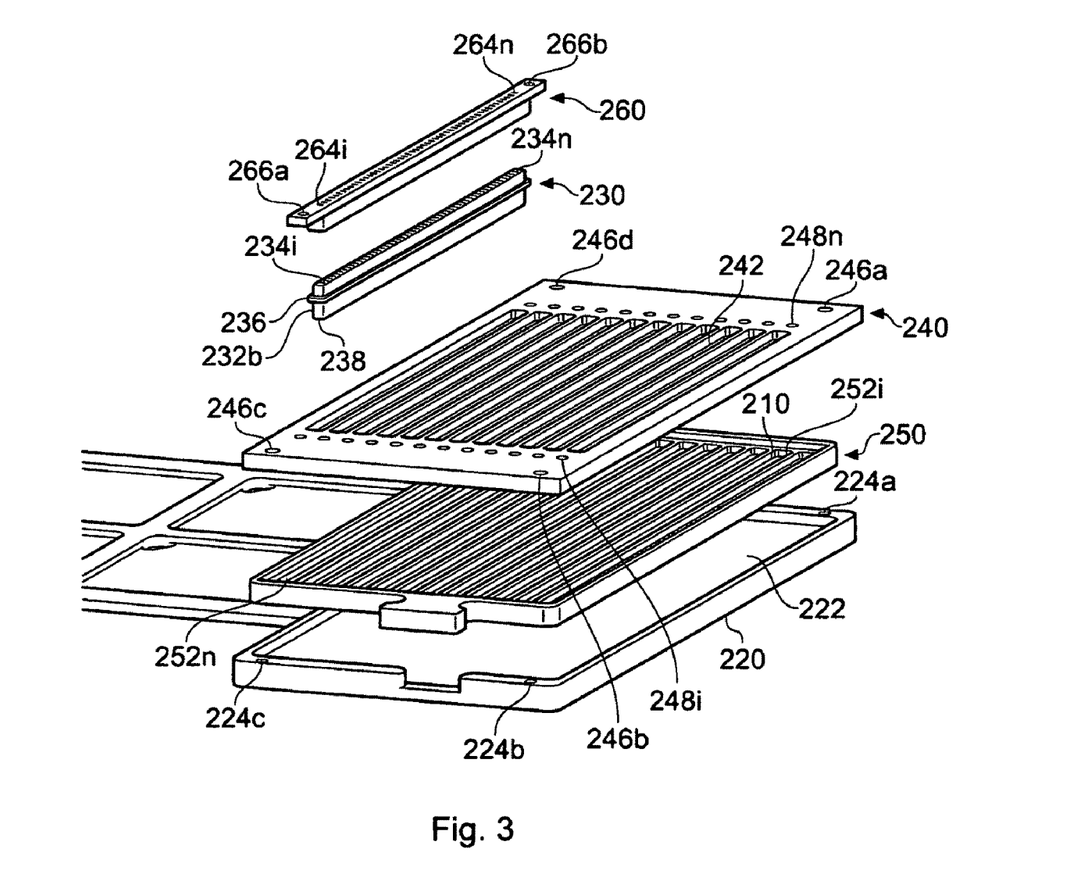
FIG. 3 shows an apparatus for adding a reagent to an analyte in an isoelectric focusing gel which is in the form of an IPG strip.

FIG. 3 is a perspective view of another apparatus which can be used to carry out the method of the invention. The apparatus shown in FIG. 3 is suitable for use with isolectric focusing gels, in particular IPG strips such as Immobiline™ DryStrip gels (GE Healthcare). The IPG strip (not shown), consisting of a plastic base sheet supporting a coating of polyacrylamide gel (210), is placed within a recess (252) of a retainer (250) which is an electrophoresis manifold. The retainer (250), which is typically made of a plastic material, may consist of a plurality of recesses (252 i-n), twelve being shown in the example of FIG. 3, such that a plurality of IPG strips may be processed at the same time. Following electrofusing of an analyte in the IPG strip, the retainer (250) together with the strip is located in a predefined position within a recess (222) in the top surface of the base plate (220). The base plate may be made of a plastic or metal material. A multiwell template (230), similar in construction to that described above in FIGS. 1 & 2, comprises a plurality of open-ended chambers (234i-n) and is inserted in an opening (242) in a top plate (240) such that it supported by its flange (236) on a ledge (not shown) surrounding the opening (242). The multiwell template (230) and the top plate (240) are typically made of a plastic material but may be made of other materials such as a metal. It will be understood that a plurality of multiwell templates (230) may be positioned in the top plate (240) in the manner described; thus, for example, in the example shown, twelve multiwell templates (230) can be positioned within the top plate (240).

Once it is positioned within the top plate (240), the multiwell template (230) is lowered or moved onto the surface of the gel (210), such that the tapered portion (232b) of the body of the template compresses the gel (210) such that the base (238) of the template comes into close proximity to the plastic sheet supporting the gel (210). In this position, a well is defined with the plastic sheet or gel forming the base and the walls of the template defining the walls of the well.

It will be understood that the multiwell template (230) may be lowered or moved onto the gel (210) to form a plurality of wells thereon before the template (230) is inserted into the top plate (240). The multiwell template can then be secured into position relative to the top (240) and bottom (220) plates by use of the fastening means in the top (246 a-d) and bottom (224 a-d; d not shown) plates; for example, in FIG. 3, screws (not shown) could be used to affix the plates together.

A securing strip (260) is positioned over the top of the multiwell template (230) such that the openings (264i-n) in the strip (260) overlap and correspond to the positions of the open ended chambers (234 i-n) in the template (230). The securing strip (260) may then lock the template (230) into a predefined position by affixing it to the top plate (240) by use of the fastening means in the strip (266 a-b) and the top plate (248 i-n); such fastening means may take the form of openings in the securing strip (266a-b), screw bores in the top plate (248 i-n) and the use of one or more screws of appropriate bore. Alternatively the securing strip may be formed integrally with a multiwall template.

Figure 4:
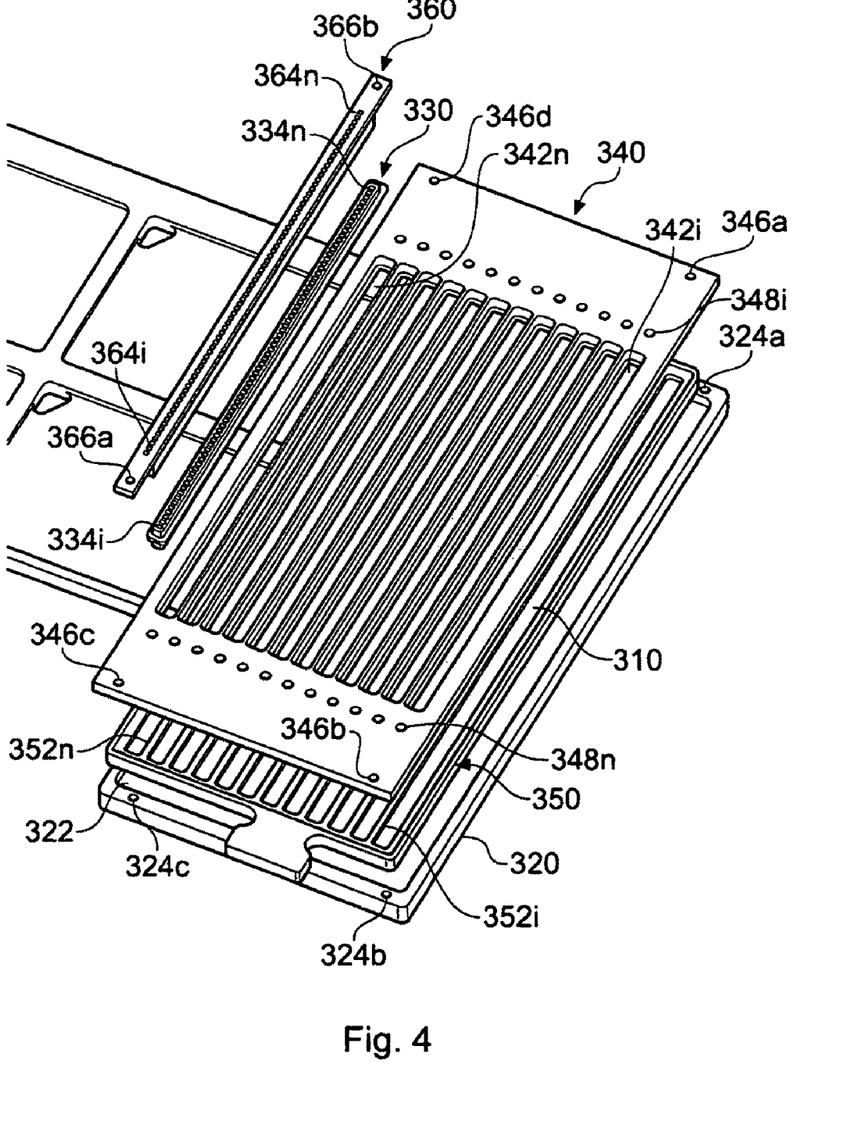
FIG. 4 is a plan perspective of the apparatus of FIG. 3.

FIG. 4 is a plan perspective of the apparatus of FIG. 3, where each of the component parts has the same features as described above for FIG. 3. Thus the apparatus consists of a base plate (320) having a recess (322) and fastening means (324 a-d, d not shown). A retainer (350) in the form of an isoelectric focussing manifold holds a number of IPG strips (not shown) within a series of recesses (352 i-n) consisting of a plastic sheet supporting a polyacrylamide gel (310). The top plate (340), made of a plastic material, consists of a plurality of openings (342 i-n) corresponding to the positions of the IPG strips within the retainer (310). Fastening means (346 a-d; and 348 i-n), corresponding to those present in the base plate (324 a-d) are present in the top plate (340). The multiwell template (330) comprises a plurality of open ended chambers (334 i-n). The securing strip (360) consists of a number of openings (364 i-n) corresponding to the position of the open-ended chambers (334i-n) in the template (330) and fastening means (366 a & b).

The apparatus of FIG. 4 may be used in the same way as described above in connection with FIG. 3 to add a reagent to an analyte in a gel.

Figure 5A:
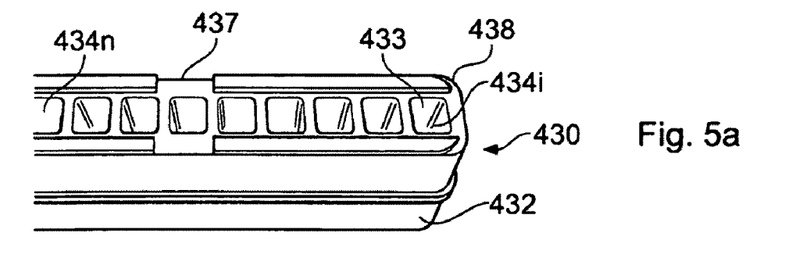
FIG. 5a is an underside view showing the base of the template featuring a plurality of open-ended chambers and FIG. 5b is the same view but with an IPG strip in position on the base of the template.

FIG. 5a is a view of the base (438) of a multiwell template (430) which is used according to the method of the invention. The open-ended chambers (434 i-n) are defined by a series of walls (433) throughout the body (432) of the template (430). Recesses or notches (437) on the base of the template (430) are used to place the template (430) onto protrusions in the retainer (not shown) which holds the IPG strips, and thus to locate the template (430) in a predefined position relative to the IPG strip.

Figure 5B:
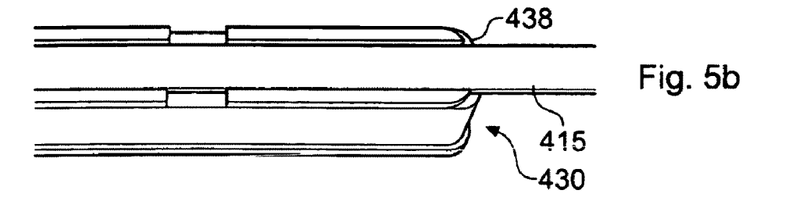

FIG. 5b shows the plastic sheet (415) of an IPG strip positioned on the base (438) of the multiwell template (430). In the perspective view shown, the gel cannot be seen because it is on the underside of the sheet (415) and is in contact with the base (438) of the template (430). In this position, the base of the sheet (415) within each chamber (434) forms the base of a well and the walls of the chamber act as the walls of a well.

Figure 6:
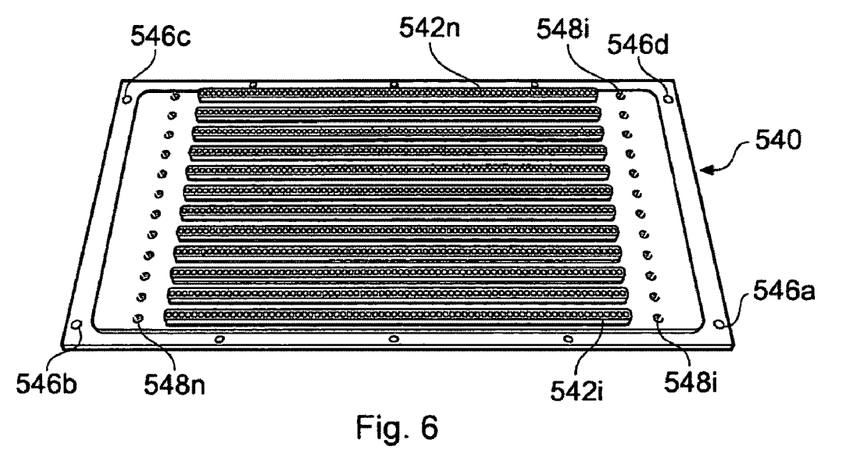
FIG. 6 shows a top plate of the apparatus illustrated in FIGS. 3 & 4 in which the multiwell templates have been inserted.

FIG. 6 shows a plan perspective of a top plate (540) which is made of steel. The openings (542 i-n) for receipt of the multiwell template (shown in position), together with fastening means for affixing to the base plate (546 a-d) and for affixing to the securement strip (548 i-n), are illustrated in the diagram.

Figure 7A:
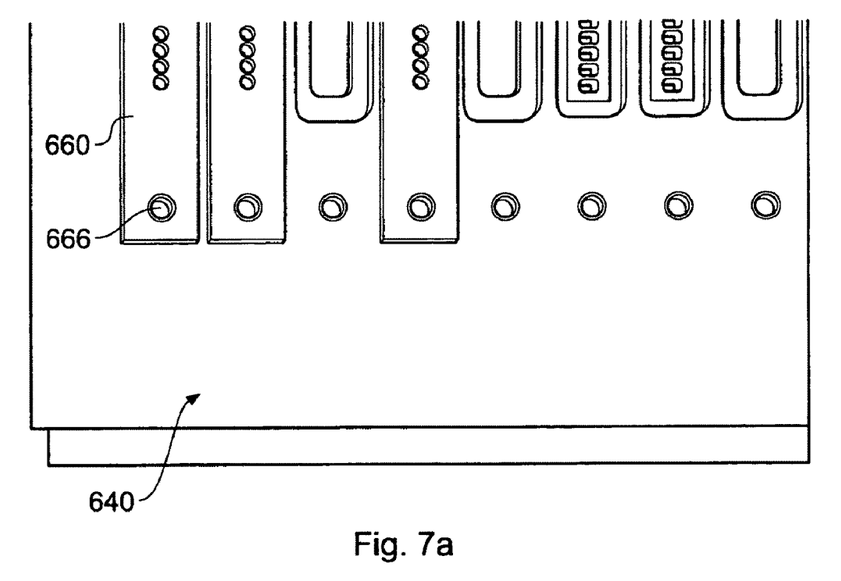
FIG. 7a is a plan view giving details of a top plate and securing strip for use in the method of the invention.

FIG. 7a is a plan view showing details of a top plate (640) used in the method of the invention in which the securing strip (660) has been positioned to affix the multiwell template (not shown) to the top plate (640). The fastening means (666), in the form of openings, are shown and co-locate with those of the retainer (not shown) in the top plate (see 548 i-n in FIG. 6).

Figure 7B:
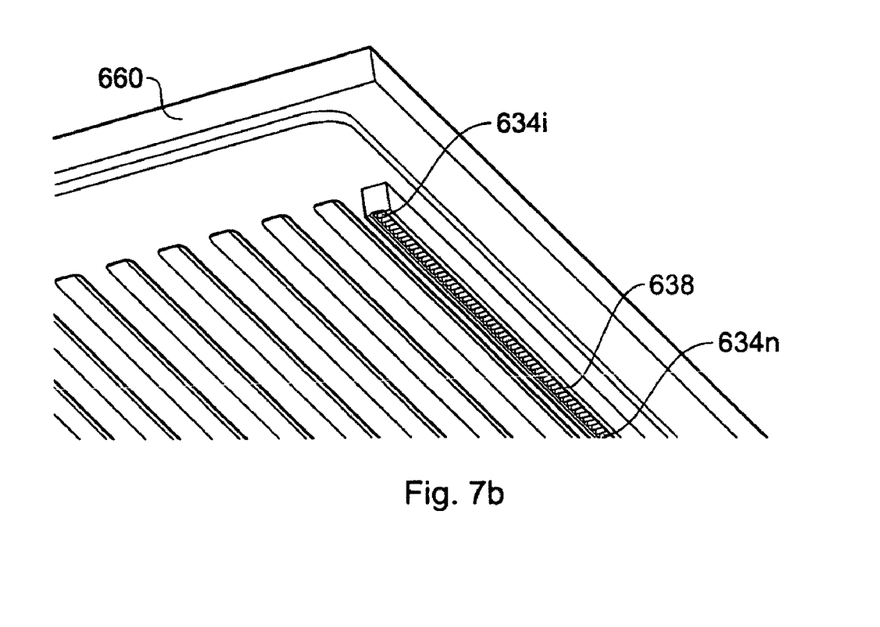
FIG. 7b is an underside view of a top plate with the multiwell template positioned within it.

FIG. 7b is an underside view showing details of the arrangement given in FIG. 7a. The base (638) of the tapered second portion of the multiwell template, which protudes from the lower surface of the top plate (660), is seen clearly from this angle. It is this base (638) which compresses the gel, each open-ended chamber (634i-n) forming a well with the gel or the base sheet (not shown) of the gel.

Figure 8:
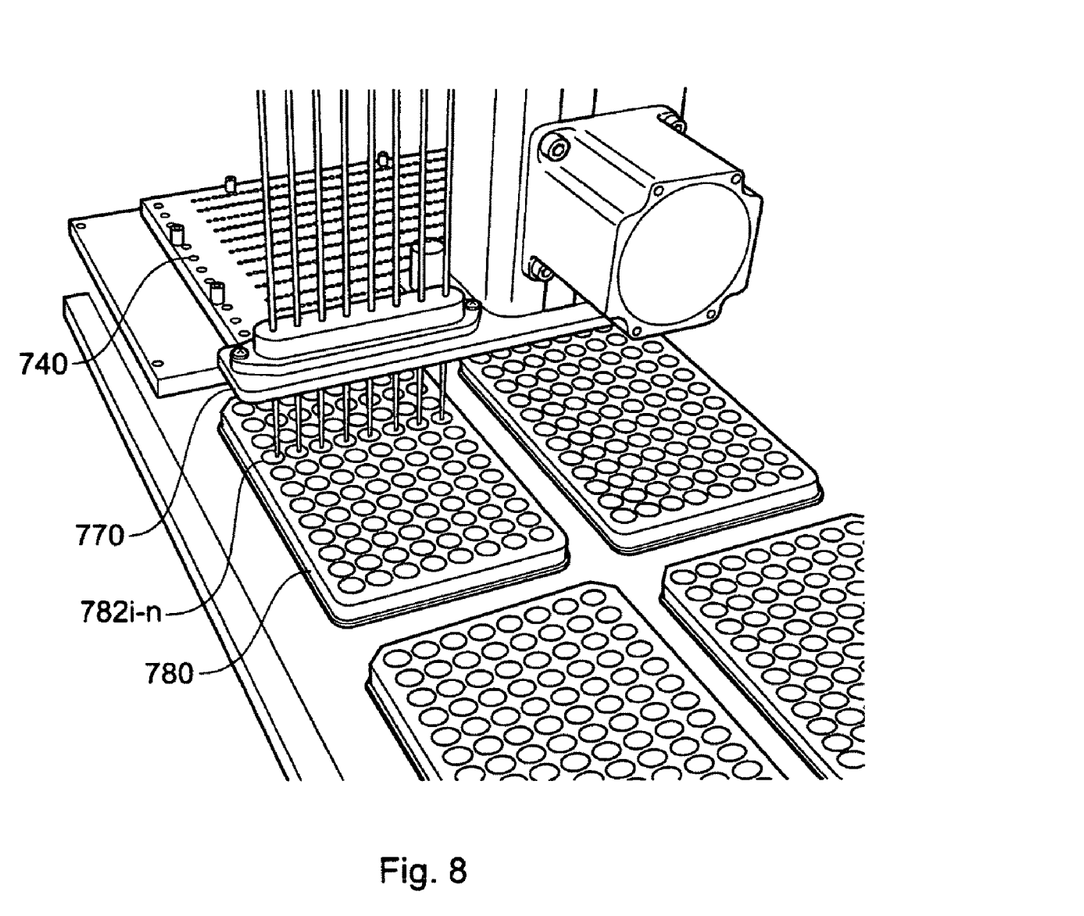
FIG. 8 shows an automatic eluting system according to the present invention.

FIG. 8 shows an automatic eluting system according to the present invention. Following electrophoresis of a sample on a gel, for instance an IPG strip, a plurality of wells is formed and buffer added to each well using the method of the invention as described above. The gel in each well is then eluted with the buffer to extract the analyte (such as a peptide) and the resulting eluant transferred to a reaction vessel for further processing/analysis. FIG. 8 shows an eight channel eluting probe (770) in the process of transferring eluant from the wells present in the top plate (740) of the apparatus of the invention to wells (782 i-n) in a microtitre plate (780). The system is under the control of a computer (not shown). The number of wells formed in the IPG strip typically correspond to the number of wells across the length or breadth of the microtitre plate (e.g. they are a multiple of 8 or 12 for a 96 well microtitre plate) or a fraction of these numbers (e.g. 2, 3, 4, 6).

SPECIFIC EXAMPLES

Isoelectric Focusing, Fluorescence Analysis and Extraction of Peptides 0.5 mg of a tryptic digest sample from Saccharomyces cerevisiae, Type II, was mixed with 5 µg of each of the pI-markers '3.73', '4.25' and '4.54'. A 'pI-marker' is a fluorescently labelled peptide with known isoelectric point that can be detected by fluorescence scanning. The fluorescent label used was Cy5™ (available from Amersham Biosciences AB; Sweden) which emission spectrum is taken at ~660 nm (Ettan DIGE System—User Manual, Amersham Biosciences AB, Sweden). A 24 cm IPG peptide strip (pH 3.4-4.8) was rehydrated overnight (~15 hours, room temperature) in 350 µl of 8M urea and sample solution. The rehydrated strip was transferred to an Ettan™ IPGphor™ manifold and isoelectric focusing was run using the following program: Gradient 500 V 1 minute, Gradient 4000 V 1.5 hours, Gradient 6000 V 1.5 hours, Gradient 10000 V 1.5 hours, Step 10000 V 12 hours (total ~150 kVhrs). Ettan IPGphor II was used as the focusing unit and the focusing was performed at 20° C.

After focusing, the IPG strip was scanned in a fluorescence scanner (Typhoon 9400 scanner, Amersham Biosciences, Sweden) at 660 nm, to determine the exact position of the fluorescent pI-markers. The Typhoon pictures were evaluated in ImageQuant and fluorescence intensity graphs established.

After scanning, the peptides in the strip were extracted from the gel into liquid fractions using the multiwell template of the invention. Thereby the pH gradient is divided into a series of discrete fractions along the strip. In this manner, the IPG strip was divided into 72 fractions at about 3 mm intervals. 50 µl water was added to each of the 72 wells, incubated at room temperature for 60 minutes and extracted peptides were then transferred to a microtitre plate in an automated manner. The elution process was repeated three times to ensure extraction and transfer of all peptides from each well. After extraction, the multiwell template was removed from the IPG strip and the device can be reused following cleaning in consecutive experiments. In the described experiment, the IPG peptide strip was once more scanned in a Typhoon scanner and the pictures were evaluated in ImageQuant.

Figure 9A:
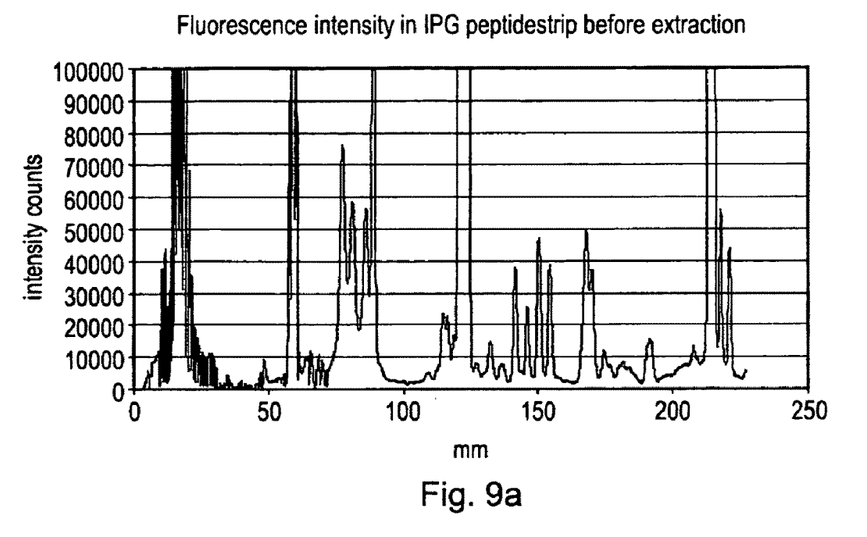
FIGS. 9a & b are fluorescence intensity scans of an IPG strip which has been used to separate fluorescently labelled peptides before (FIG. 9a) and after (FIG. 9b) elution of the gel by the method of the invention. Additional fluorescence scans of the IPG strip before and after extraction are seen in FIG. 9c, together with a scan of a microtitre plate containing the fractions eluted from the strip.
Figure 9B:
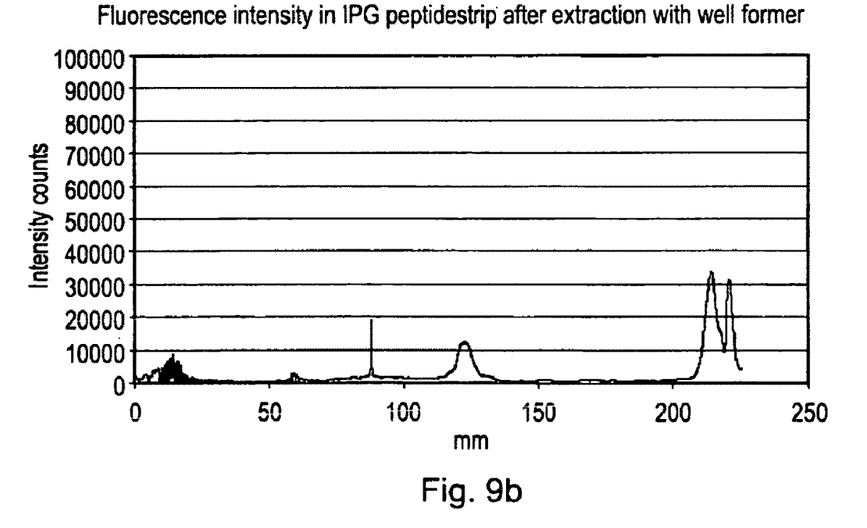
Figure 9C:
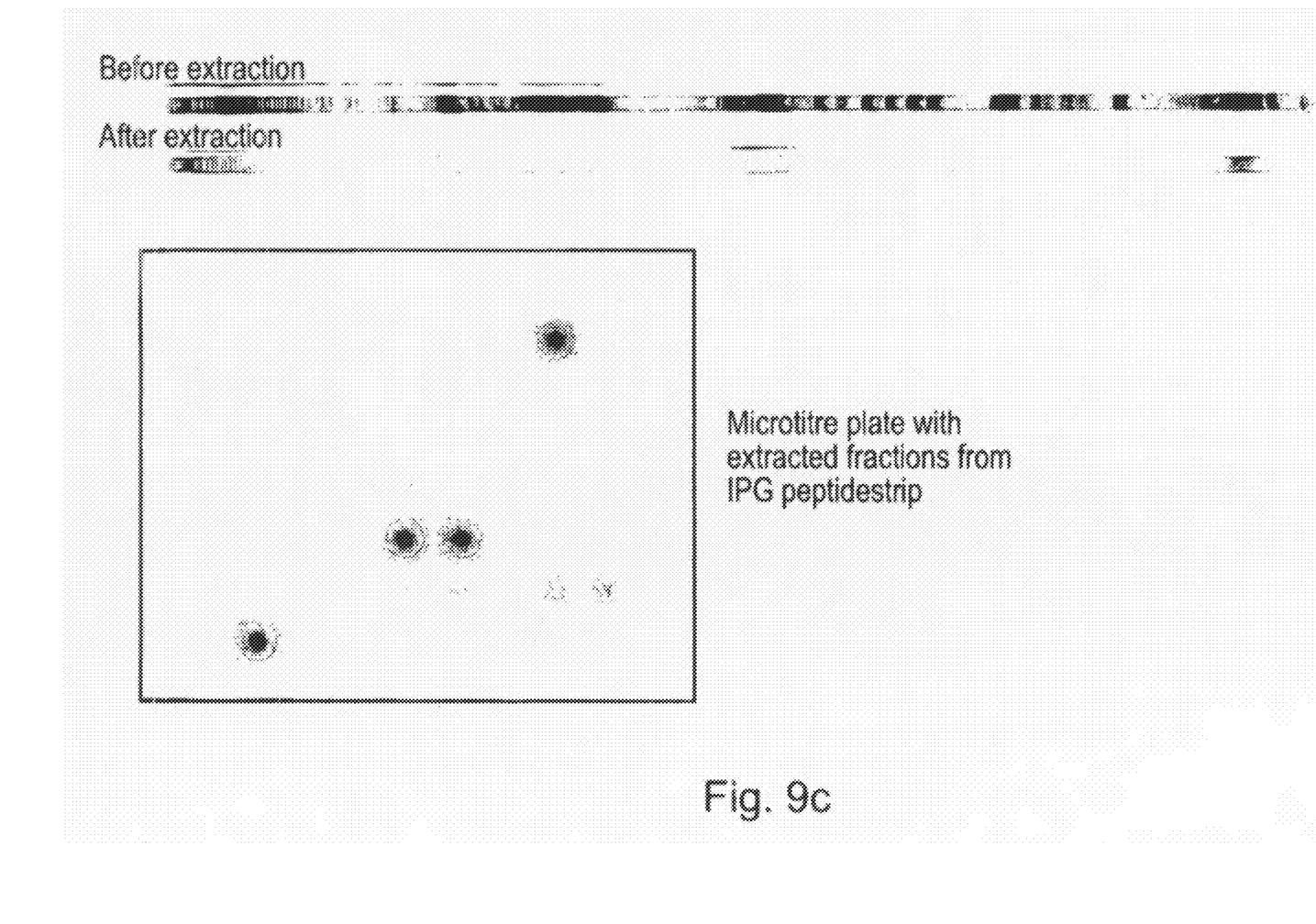

FIG. 9 shows the fluorescent intensity of the peptide IPG strip before (FIG. 9a) and after (FIG. 9b) extraction. FIG. 9c shows the scanned microtitre plate with extracted peptide samples and the strips before and after extraction, demonstrating high and low levels of fluorescence, respectively. From the Figures it is clear that the peptides have been effectively extracted from the IPG strip and are now present in the wells of the microtitre plate.

Figure 10:
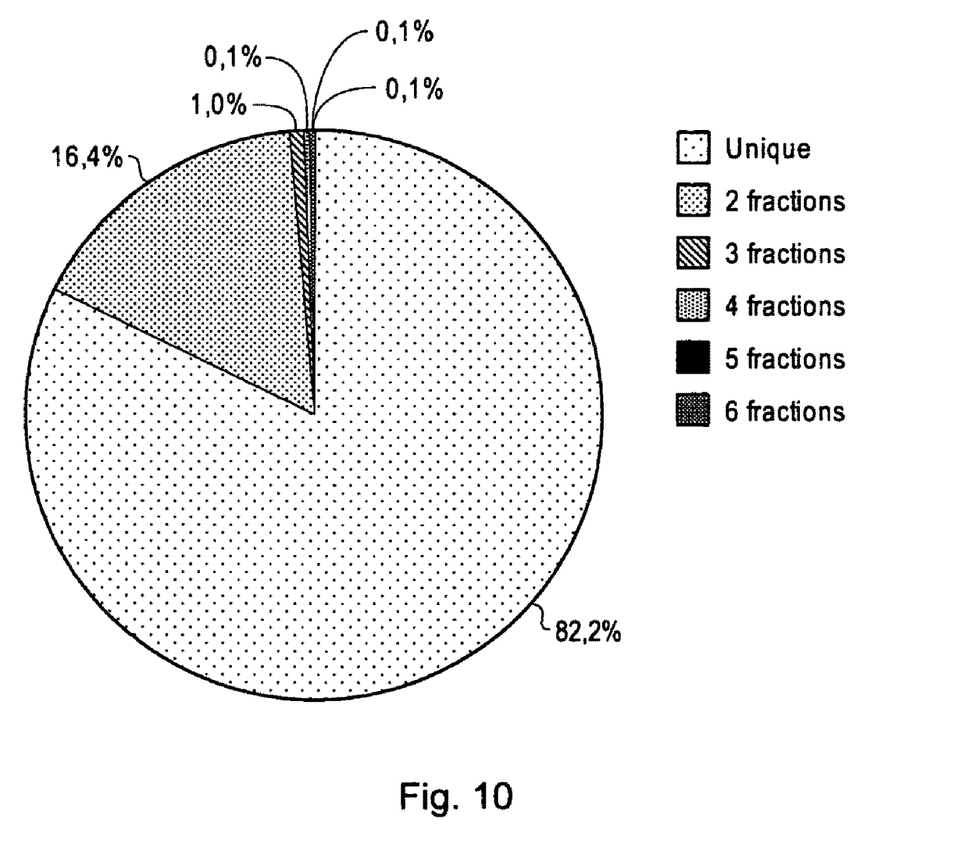
FIG. 10 is a graphical illustration of the distribution of identified peptides present in only one or several fractions extracted from a gel using the method of the invention.

FIG. 10 shows the result of a comparison between all identified peptide sequences in seven fractions next to each other on the basic end of the IPG strip. Of a total of 719 identified peptides in the seven compared fractions, 82% of the peptides were present in only one fraction and 16% in two fractions. The results of this experiment not only underline the high resolution in the IPG strip but also that there is no problem with leakage between the wells formed using the multiwell template of the invention.

The invention claimed is:

1. A method for eluting, from a gel, an analyte separated along a separation direction in said gel, the gel being arranged in an electrophoresis retainer, comprising the steps of:
   moving an apparatus for forming a plurality of elution-wells along a separation direction of the gel onto said gel, the apparatus comprises a top plate and one or more multiwell templates comprising a body having a plurality of open-ended chambers along the separation direction, each said chamber being defined by one or more walls, the one or more multiwell templates being arranged in the top plate such that it extends from the bottom surface thereof;
   securing the top plate in a predetermined position on top of the electrophoresis retainer and so that the one or more multiwell templates, when the top plate is arranged in position on the electrophoresis retainer, comes into contact with and compresses the gel to form a plurality of elution-wells along the separation direction of the gel with the gel forming a base and the individual well templates of the multiwell templates defining the walls of the wells;
   adding a liquid reagent to the one or more of said wells to form a liquid analyte reagent mixture, wherein the liquid analyte reagent mixture is capable of solubilising the analyte; and
   transferring said liquid analyte reagent mixture to a second vessel by either manual or automatic means.

2. The method of claim 1, wherein the liquid analyte reagent mixture is a buffer.

3. The method of claim 1, wherein the liquid analyte reagent mixture is an acid or an alkali.

4. The method of claim 1, wherein the liquid analyte reagent mixture is an enzyme.

5. The method of claim 4, wherein the enzyme is a hydrolase.

6. The method of claim 4, wherein the enzyme is a nuclease or a protease.

7. The method of claim 6, wherein the liquid analyte reagent mixture is a detectable moiety.

8. The method of claim 7, wherein the gel is supported on a sheet.

9. The method of claim 1, wherein said retainer comprises one or more recesses or protusions on one surface for receipt of the gel or the sheet thereon.

10. The method of claim 9, wherein said one or more recesses or protusions of the retainer additionally comprises locating means for positioning the sheet thereon.

11. The method of claim 10, further comprising the step of inserting the multiwell template into an opening in a top plate.

12. The method of claim 11, further comprising the step of affixing a securing strip over the end of the multiwell template located within the top plate, said strip comprising a plurality of openings corresponding to the positions of the open-ended chambers in the template.

13. The method of claim 1, wherein the gel is a polyacrylamide gel.

14. The method of claim 1, wherein the gel is a SDS gel or an isoelectric focusing gel.

15. The method of claim 1, wherein the body of the multiwell template is divided into a first portion and a second portion, said first portion being shaped for insertion into the opening in the top plate and a second portion being tapered to a base for moving onto the gel.

16. The method of claim 15, wherein the first and second portions are separated by a flange for supporting the multiwell template within the opening in the top plate.

17. The method of claim 1, wherein the analyte is a peptide, protein, nucleic acid or carbohydrate.

18. The method of claim 1, wherein the analyte is a protein or peptide.

19. The method of claim 1, wherein the multiwell template is moved onto the gel following the chromatographic or electrophoretic separation of the analyte within the gel.

20. The method of claim 1, wherein the liquid analyte reagent mixture is added by manual means.

21. The method of claim 1, wherein said second vessel is a well in a microtitre plate.

22. The method of claim 1, wherein the liquid analyte reagent mixture is added by an automatic liquid handling device and/or the liquid analyte reagent mixture is transferred by an automatic liquid handling device.

23. The method of claim 22, wherein said automatic liquid handling device is under control of a computer.

* * * * *